(12) United States Patent
Jelliffe et al.

(10) Patent No.: US 6,896,660 B2
(45) Date of Patent: May 24, 2005

(54) THERAPEUTIC DECISIONS SYSTEMS AND METHOD USING STOCHASTIC TECHNIQUES

(75) Inventors: Roger Jelliffe, Pasadena, CA (US); William Shoemaker, Valley Center, CA (US); David Bayard, Glendale, CA (US); Andreas Botnen, Oslo (NO)

(73) Assignee: University of Southern California, Los Angeles, CA (US)

( * ) Notice: Subject to any disclaimer, the term of this patent is extended or adjusted under 35 U.S.C. 154(b) by 98 days.

(21) Appl. No.: 10/177,655

(22) Filed: Jun. 19, 2002

(65) Prior Publication Data

US 2003/0060690 A1 Mar. 27, 2003

Related U.S. Application Data

(60) Provisional application No. 60/299,578, filed on Jun. 19, 2001.

(51) Int. Cl.[7] .............................................. A61B 5/02
(52) U.S. Cl. ...................... 600/481; 600/301; 128/923
(58) Field of Search ................. 128/920, 923, 128/924, 925; 600/300–301, 481–508

(56) References Cited

U.S. PATENT DOCUMENTS

| | | | | |
|---|---|---|---|---|
| 4,858,614 A | * | 8/1989 | Stevens et al. | ............. 600/543 |
| 4,930,506 A | * | 6/1990 | Ullrich | ........................ 600/326 |
| 5,309,917 A | | 5/1994 | Wang et al. | |
| 5,971,934 A | | 10/1999 | Scherer et al. | |
| 6,063,026 A | * | 5/2000 | Schauss et al. | ............. 600/300 |
| 6,193,654 B1 | * | 2/2001 | Richardson et al. | ........ 600/300 |
| 6,398,728 B1 | * | 6/2002 | Bardy | ........................ 600/300 |
| 6,440,067 B1 | | 8/2002 | DeLuca et al. | |
| 6,463,930 B2 | * | 10/2002 | Biondi et al. | .......... 128/204.21 |
| 6,607,480 B1 | * | 8/2003 | Bousseljot et al. | ......... 600/300 |
| 6,622,036 B1 | * | 9/2003 | Suffin | ........................ 600/544 |

* cited by examiner

*Primary Examiner*—Robert L. Nasser
*Assistant Examiner*—Patricia Mallari
(74) *Attorney, Agent, or Firm*—Fish & Richardson P.C.

(57) ABSTRACT

Patients are evaluated in terms of various physiological parameters such as hemodynamic parameters. Covariate information indicative of the patient's individual characteristics may also be determined. A state variable indicative of the patient's characteristics is determined. This state variable is used to compare the patient to other patients in the database. The other patients in the database are evaluated in terms of similar parameters and their probability of survival as well as different treatments and the probability of survival based on those different treatments. The patient may be simply evaluated based on the database or a proper course of treatments may be determined based on the database.

21 Claims, 2 Drawing Sheets

THERAPEUTIC DECISIONS SYSTEMS AND METHOD USING STOCHASTIC TECHNIQUES

CROSS-REFERENCE TO RELATED APPLICATIONS

This application claims benefit of U.S. Provisional Application No. 60/299,578, filed Jun. 19, 2001.

BACKGROUND

The determination of how to treat a highly ill patient can be very difficult, especially under the chaotic and emotional conditions that may exist in the conditions surrounding around such a highly ill patient. For example, such an ill patient may be treated in the context of an emergency situation such as shock, high risk surgery, trauma and other acute conditions requiring emergency treatment. It has been found by the inventors that diagnosis errors commonly occur under those emergency conditions.

It is also difficult, especially in these emergency situations, to evaluate the timing of a given therapy. A given therapy that improves the outcome at one point may actual produce harm at a different point, or when used in the wrong amount for the wrong situation. For example, fluid therapy used at the initial phase of resuscitation may be critical. However, use of excess fluids may lead to pulmonary edema and cardiac failure. Such errors can be lethal in emergency situations. Moreover, many different injuries, shock being one, may be easy to recognize in late stage when therapy is often ineffective. If hypovolemia is inferred from tachycardia, hypotension, and falling hematocrit, these superficial manifestations of shock may be overtly corrected by transfusions, fluids, and vasopressors, but still without adequately restoring the underlying circulatory functions.

It has been found that effective resuscitation of acute life-threatening emergencies achieves optimal physiological goals as early as possible. When circulatory mechanisms are identified earlier and treated more vigorously to specified physiologic target goals, outcomes are improved.

The incidence, mortality, morbidity, and costs of life threatening illnesses and injuries are extraordinary. Among the 1.9 million deaths annually, about half are from acute illness associated with shock and lethal organ failure. There are over 34 million surgical operations annually in the U.S., with an overall mortality of 1%, but high-risk surgical patients have mortality between 25 and 33%. Postoperative deaths are often due to adult respiratory distress syndrome (ARDS), which has an incidence of 150,000, a mortality of around 40%, consumes an average of two weeks in the ICU, and in this country costs about $1,950,000,000 annually. There are about one-half million septic patients, of whom 40% develop shock, with 50% mortality. Septic shock is the 13th leading cause of death, and the most common cause of ICU deaths. Hospital costs for septic shock are over 5 billion dollars annually.

Conventionally, shock is classified as hemorrhagic, traumatic, postoperative, neurogenic, and distributive or septic. Usually this classification is applied to the later, fully developed, clinical syndromes of shock. Analysis of circulatory mechanisms when patients are admitted to the ICU in the late stage, after organ failure has occurred, is extremely complex because of the many interacting clinical, physiological, and immunochemical problems. Over 12 separate cascades of chemical mechanisms have been described. Many of these have been considered to be the cause of shock, and major efforts have been expended to reverse them. Of the 11 or more large scale, multicenter, randomized clinical trials, only the recombinant human activated protein C (drotrecogin alfa activated) has shown improvement in mortality, which decreased from 30.8% in the placebo control group to 24.7% in the protocol group, a decrease of 6.1% (38). The many interacting immunochemical mechanisms make the problems of sorting out causal relationships more difficult, and the therapy less effective, after organ failure and sepsis have become established in the late stages of critical illness.

There are six commonly used outcome predictors: the Acute Physiology and Chronic Health Evaluation (APACHE), Glasgow Coma Scale (GCS), the penetrating abdominal injury (PATI) score, the Therapeutic Intervention Scoring System (TISS), The Revised Trauma Score and Injury Severity Score (TRISS) and the Trauma score. All of them assess categories of patients in terms of probable mortality. The are not intended to predict mortality risk for a specific single patient. Those systems are rarely used for guiding actual patient care. They find their greatest use as a tool for administrative and management research and decisions. Longitudinal scoring on successive days may reflect continuous improvement, but has no physiologic or therapeutic relevance for any specific individual patient. Moreover, none of them identify specific underlying physiologic mechanisms or problems as does the present approach. In addition, none of them considers specific therapeutic recommendations to be suggested, real-time, to the physician. Finally, none are able to recommend titration of therapy to alleviate the underlying hemodynamic problem or to achieve optimal goals.

BRIEF DESCRIPTION OF THE DRAWINGS

These and other aspects will now be described in detail with reference to the accompanying drawings, wherein.

SUMMARY

The present technique, in contrast to the above, defines techniques for detecting, and optimally correcting, for each individual patient, in a real-time manner, the initiating hemodynamic mechanisms of shock and circulatory dysfunction, in conjunction with a new outcome predictor and real-time guidance and decision support for optimizing therapy. This is very different from the above scoring systems currently in use, which provide only reports concerning prognosis.

The present invention teaches a system and machine of patient monitoring of various parameters and decision support that is guided by a stochastically analyzed operation. This operation can evaluate and optimize the therapy that is used especially in such difficult situations.

Another aspect is an outcome predictor that calculates the probability of survival for any individual patient. This predictor, in an embodiment, is based on a program of stochastic/probability analysis developed from a database that includes clinical conditions.

An embodiment determines the patients state (S) using a specified mathematical criteria, and determines patients in the database most similar to the patients state. Individualized therapy that maximizes the probability of survival may be determined from those other patient states that are closest to the patient's state.

DESCRIPTION

Many or most deaths in acute illnesses are based on circulatory factors. An aspect of this application describes characterizing a patient based on hemodynamic parameters and comparing those parameters to previously obtained information in a database. While the present embodiment describes hemodynamic parameters, it should be understood that other parameters besides hemodynamic parameters can be analyzed. Hemodynamic measurements, however, may be specifically advantageous since many previous studies and clinical trials have established relationships between such hemodynamic parameters and patient results (where patient results may include survival, long term injury, or other results). Also, noninvasive monitoring technology is available in many different forms for obtaining hemodynamic measurements.

Figure 1:
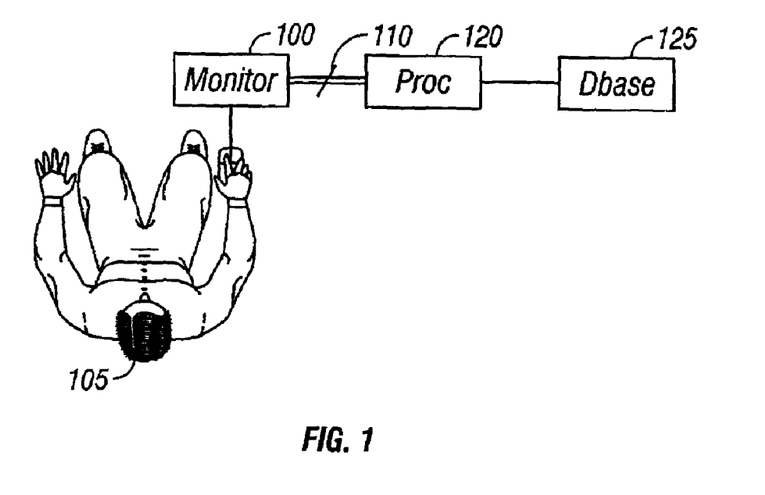
FIG. 1 shows a block diagram of a patient being monitored, and the system described herein.

An embodiment shown in FIG. 1. A monitoring part 100 monitors various parameters of the patient. The monitoring may be both noninvasive and invasive, although noninvasive monitoring may be preferred. As described herein, the monitor may monitors various characteristics including cardiac index, blood pressure, arterial and cutaneous oxygen, carbon dioxide level, and other parameters as discussed. Multiple different parameters may be monitored. The output parameters 110 represents all of these different parameters. Moreover, while the monitoring element 100 is shown as being in a single location, it should be understood that the monitoring may be carried out at multiple different locations.

The output parameters 110 are coupled to a processor 120, which receives the data and carries out operations using the data as described herein. The processor 120 is also associated with a database 125. The database includes various information about the patients that have been treated in the past. Again, further details on this are described herein. Both the processor 120 and database 125 can be either local, or may be remote from the patient, in which case the link that carries the data 110 may be a network connection e.g. the Internet.

The database includes information about other patients as a function of all or some of the monitored variables. The database and processor determines mathematically the state of this particular patient by finding the mathematical nearest neighbors. These mathematical nearest neighbors can also be analyzed to determine what percentage of these patients live or die, and/or how successful specified treatments on these kinds of patients have been in the past. This can be used, in turn, to make decisions about what kind of therapy might be the best kind of therapy both in the short-term and in the long term.

All measurements are preferably started with the patient's admission to the emergency department (ED). When the paramedics radio the ED that a trauma patient is coming in, the trauma team on call is alerted and is ready in the ED to receive the patient. The patient is then followed to the radiology department, the operating room (OR), the intensive care unit (ICU), and ultimately to the patient's survival or death at hospital discharge. In surgical patients, the noninvasive hemodynamic measurements are started with onset of anesthesia, continued throughout surgery, and followed in the ICU, step-down units, and hospital floors.

Monitoring element 100 may monitor the following:

Bio impedance. This is a device that measures the biological impedance of the user. Various injuries, such as chest wall edema or chest tubes may cause the electrical signals to be distorted, but compensation for this distortion can be made.

Biological impedance may be measured using an improved continuous noninvasive impedance system (IQ device) has developed by Wang et al at Drexel University and marketed by Wantagh, Inc., Bristol Pa. They use noninvasive disposable prewired hydrogen electrodes positioned on the skin, three EKG leads placed across the precordium and left shoulder, and a 100 kHz, 4 mA alternating current passed through the patient's thorax by the outer pairs of electrodes. The low voltage is sensed by the inner pairs of electrodes. The voltage sensed by the inner electrodes captures the baseline impedance (Zo), the first derivative of the impedance waveform (dZ/dt), and the EKG. The EKG and the bioimpedance signals are filtered with an all-integer-coefficient method that simplifies computations and decreases signal processing time.

The signal processing technique is based on time-frequency distribution technology that provides high signal-to-noise ratios that increases the speed of signal processing and permits essentially real time operation without deterioration of accuracy. It shows the relationship between the time, frequency, and power of the signal that would otherwise be unobtainable from the standard fast Fourier transform. This is particularly important in identification of opening and closing of the aortic valve ("B" and "C" points), which are often buried in artifacts that make them difficult to identify. Variables available for display and printout include: cardiac output and index, stroke volume, Zo (baseline impedance), MAP (mean arterial pressure), HR (heart rate), systemic vascular resistance, dZ/dt max (maximum increase in impedance rate), pre-ejection period, ventricular ejection time, acceleration index, dz2/dt2, and end-diastolic volume.

Pulse oximetry (machine from Nellcor, Pleasanton, Calif.) continuously measures arterial oxygen saturation (SaO2). Appreciable changes will be noted and confirmed by the standard in vitro blood gas analysis. Pulse oximetry has been extensively evaluated and is routinely used. The pulse oximetry may be used to Compare Pulse Oximetry with In Vitro Hemoglobin Oxygen Saturation, and to Compare Transcutaneous Oxygen Tension ($PtcO_2$) and Oxygen Consumption. Oxygen consumption ($VO_2$) values may be compared with simultaneous $PtcO_2$ at the initial baseline period, the nadir, and after resuscitation. The $PtcO_2$ nadir occurred an average of 12.1±7.7 min (p<0.05) before the $VO_2$ nadir, indicating that while both methods reflect tissue perfusion, $PtcO_2$ decreases occur first, and provide an earlier warning of inadequate tissue perfusion.

Survivor and Nonsurvivor Patterns in High-Risk Surgery and Trauma.

Therapeutic Effects of Blood, Albumin, Crystalloids, Dopamine, and Dobutamine, evaluated by Invasive Monitoring.

Noninvasive Monitoring of the Effects of Packed Red Cells, Albumin, and Crystalloids.

Comparison of Temporal Patterns of Hemodynamic Data with Immunochemical Mediators.

Transcutaneous Oxygen and Carbon Dioxide for Estimation of Tissue Perfusion.

Standard transcutaneous oxygen tension (PtcO2) measurements (Novametrix Medical Systems, Inc., Wallingford Conn.) will be continuously monitored throughout the observation period. Previous studies have shown well the ability of PtcO2 to reflect tissue oxygen tension. PtcO2 reflects delivery of oxygen to the local area of skin; it also parallels the mixed venous oxygen tension except under late or terminal conditions where peripheral shunting may lead to high mixed venous hemoglobin saturation (SvO2) values (18). It uses the same Clark polarographic oxygen electrode routinely used in standard blood gas analyses (15,18–20). Oxygen tensions are determined in a representative area of the skin surface heated to 440C to increase emissivity of oxygen across the stratum corneum, and to prevent vasoconstriction in the local area being measured (19). Transcutaneous CO2 monitoring (Novametrix Medical Systems, Inc., Wallingford Conn.) of the skin surface will be continuously monitored by the standard Stowe-Severinghaus electrode (14) in the same sensor unit.

Covariate information may also be obtained.

The following 30 covariates may be measured: 1) age, 2) gender, 3) preoperative, intra-operative, and postoperative estimated blood loss, 4) blunt or 5) penetrating truncal trauma, 6) nontruncal (extremity) injury, 7) spinal cord injury, 8) blunt or 9) penetrating cardiac injury, 10) pulmonary contusion, 11) pelvic fracture, 12) long bone fractures, 13) head injury, 14) brain death, 15) early stage (<12 h), 16) middle stage (12 to 24 h), 17) late (>24 h) stage, 18) cardiac insufficiency (reduced cardiac reserve capacity determined by responses to standardized doses of transfusions, and fluid challenges), 19) bacterial contamination, sepsis or systemic immune response system (SIRS), 20) respiratory dysfunction or failure immediately prior to the present acute illness, 21) pre-illness renal insufficiency or failure, 22) pre-illness hepatic failure, 23) nutritional insufficiency or failure, 24) uncontrolled diabetes, 25) pre-illness essential hypertension, 26) cardiac injury, blunt or penetrating, 27) cardiac arrest, 28) pregnancy, 29) Glasgow coma score, and 30) the injury severity score (ISS).

Quantitative Assessment of Continuously Monitored Noninvasive Variables as Net Cumulative Amount of Excess or Deficit may be an important factor. While monitored values can be directly observed, many show considerable variability, which may obscure the underlying pattern. To overcome this problem, we calculate the net cumulative excess or deficit of physiological variables by integrating the areas between the curves of monitored data and selected normal or "optimal" values. This provides a quantitative measure of the overall deficit in cardiac, pulmonary, and tissue perfusion function. This may provide a more useful early evaluation of the patient's physiological responses than simply following empirical scoring systems (Apache, etc.,) which are designed only for prognostic reports. Real-time suggestions concerning the best therapeutic course of action for the patient are simply beyond their scope.

Figure 2:
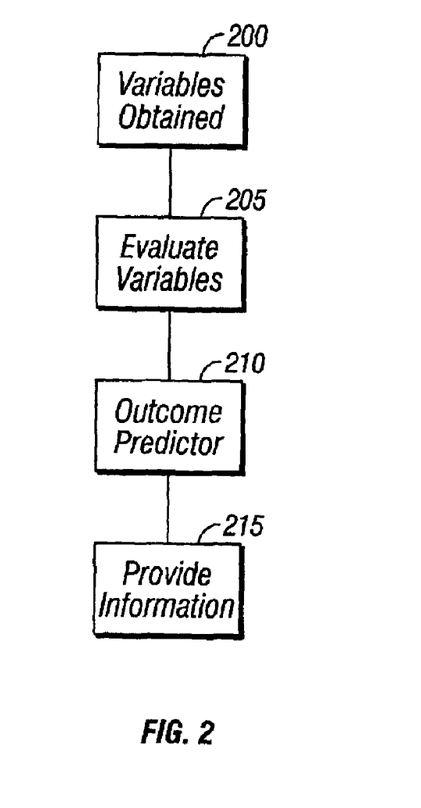
FIG. 2 shows a flowchart of the basic operation of the system.

The processor 120 may carry out a program that is described in the flowchart of FIG. 2. At 200, all of the variables described above may be obtained, as well as other variables which are described herein. These variables are preferably obtained by noninvasive techniques, although they can alternatively be obtained by more invasive techniques. At 205, each of these variables is evaluated. The evaluation may be carried out by comparing the variable with its normal or optimum value and a temporal pattern during the observation. The variable may be mathematically integrated over time versus normal or optimum variables. Net cumulative deficits or excesses are then calculated for each individual patient.

Table 1 shows the different variables and how they compared in some survivors and non survivors. The variables obtained include cardiac index, mean arterial pressure, arterial hemoglobin saturation and transcutaneous oxygen.

| Variable | Units | Optimal | Survivors | Nonsurvivors | P Value |
|---|---|---|---|---|---|
| CI | L/min/m$^2$ | 4.0 | 4.14 ± 0.02 | 3.87 ± 0.03 | 0.001 |
| MAP | mmHg | 85 | 88 ± 0.37 | 80 ± 0.69 | 0.066 |
| SapO$_2$ | % | 98 | 99 ± 0.05 | 96 ± 0.26 | 0.001 |
| PtcO$_2$/FiO$_2$ | | 200 | 206 ± 2.9 | 93 ± 2.6 | 0.001 |

The mean values similarly show this trend:

| Variable | Units | Survivors | | Nonsurvivors | | P value |
|---|---|---|---|---|---|---|
| | | Mean | SEM | Mean | SEM | |
| CI | L/min/m$^2$ | +81 | 52 | −232 | 138 | 0.007 |
| MAP | mmHg | −10 | 12 | −57 | 24 | 0.078 |
| SapO$_2$ | % | −1 | 0.3 | −9 | 2.6 | 0.006 |
| PtcO$_2$/FiO$_2$ | | +313 | 87 | −793 | 175 | 0.001 |

In an experiment, out of 103 patients who survived their illnesses, 98 were correctly predicted to survive the illness by comparing their values with other similar patients. Of the 48 who did not survive, 30 were correctly predicted not to survive. This compares with previous studies in which much poorer results were obtained. Thus far, using this approach, those with outcome probability is greater than 80 percent have survived, and always outcome probability is less than 35 percent have died. This can be used as a basis for determining a likelihood that the patient will survive based on the treatments and results for other patients.

In general, the specific monitored goals of therapy will be based on the current empirical findings of the survivors present in our current patient database: cardiac index >4.5 L/min/m$^2$; systolic blood pressure >120 mmHg; pulse oximetry >96%; transcutaneous oxygen PtcO$_2$/FiO$_2$ ratio >200; heart rate <100 beats/min. Packed red cell transfusions will be given to maintain Hct >30% or hemoglobin concentrations >10 g/dL. The time to obtaining these goals, the amount and type of fluids will be noted.

Figure 3:
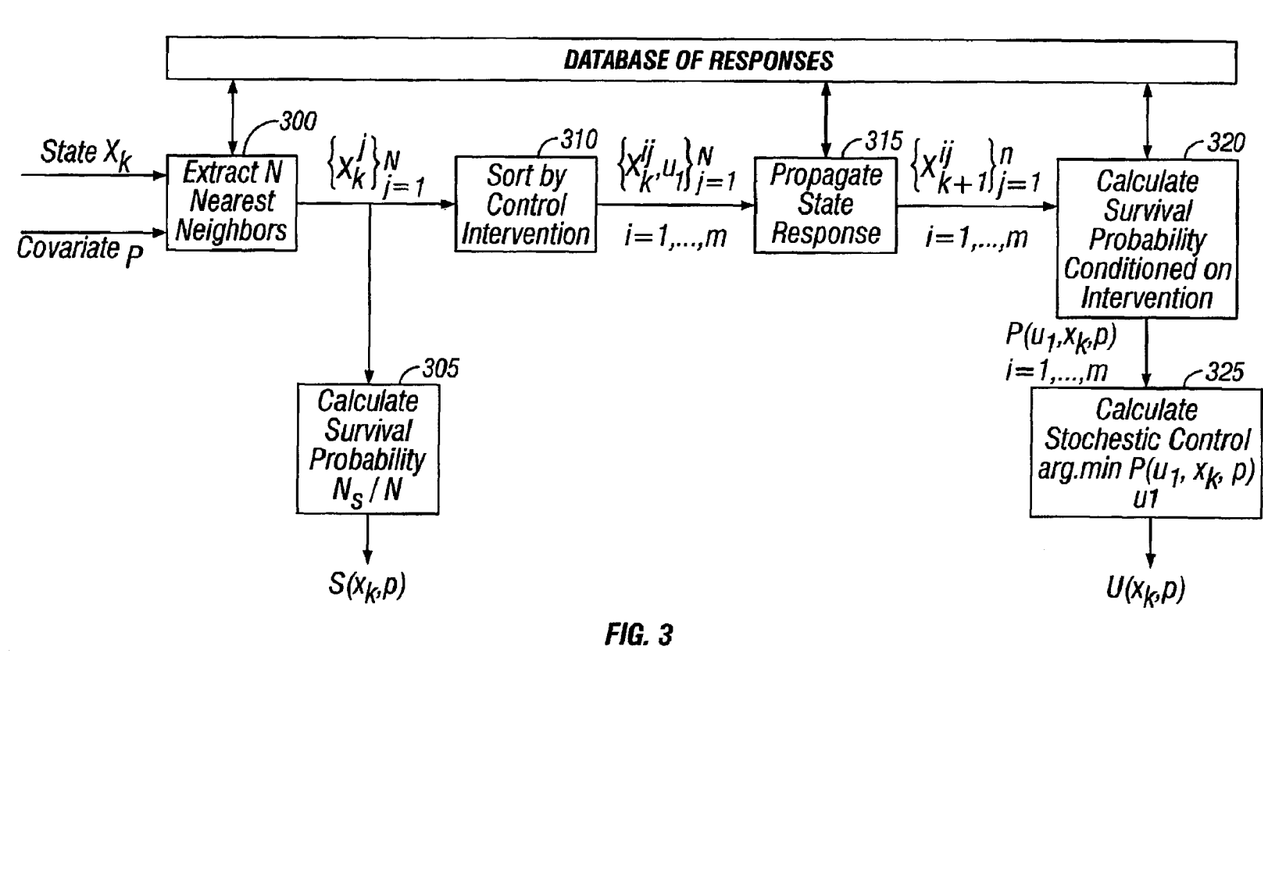
FIG. 3 shows a flowchart of relationship with the database.

At 210, an outcome predictor is used with the variables. The outcome predictor uses the probability of survival as being a measure of the severity of illness before and after treatment of hemodynamic problems that may contribute to the non survival pattern. Correction or failure to correct each mechanism by the specific therapy at each temporal stage during the acute illness is taken as a measure of the reversibility of the injury mechanism. Then, the predicted changes in outcome are compared with actual survival or death at hospital discharge. The specific flowchart of the outcome predictor is shown in FIG. 3. The flowchart operates on dynamic program based on the "state" of the patient at any time, shown as the variable X. Based on this state, an optimal therapeutic policy is determined that has, on the average, proven to work best for similar patients in similar conditions that are recorded in the database 125. The term 'similar' here means a group of patients who have the same diagnoses who share the same set of specified covariates, and have similar hemodynamic states.

This state of the patient at any time is therefore defined in terms of primary diagnoses, covariates, and hemodynamic measurements. x(t) is referred to as the state vector at time t. This is defined in terms of the hemodynamic measurements, their derivatives, and their integrals.

Assuming that there are L different kinds of measurements taken on a given patient. The set may include for example cardiac index, blood pressure, pulse oximetry, transcutaneous oxygen and $CO_2$ tensions. Each measurement I is denoted as $y_L$. The state vector is defined as a concatenation of the value $y_L$ as well as its derivative or or each measurement type, denoted as $y_l$ define the state vector as a concatenation of the value $y_l$ itself, its first and second derivatives $y_l'$, $y_l''$, and its first integral $\int y_l dt$, as follows:

$$x(t_k) = \left[ y_1(t_k), y_1'(t_k), y_1''(t_k), \int_0^{t_1} y_1 \, dt, \ldots, \ldots, \ldots, y_L(t_k), y_L'(t_k), y_L''(t_k), \int_0^{t_1} y_L \, dt \right]^T \quad (2.1)$$

i.e., for L different measurement types there will be 4 L states. In practice, the derivatives and integrals are approximated by finite differences and sums of the time-ordered data of the database. Specifically, we will calculate the approximations.

$$y_l' \cong \frac{y_l(t_k) - y_l(t_{k-1})}{t_k - t_{k-1}} \quad (2.2)$$

$$y_l'(t_{k-1}) \cong \frac{y_l(t_{k-1}) - y_l(t_{k-2})}{t_{k-1} - t_{k-2}}$$

$$y_l''(t_k) \cong \frac{y_l'(t_k) - y_l'(t_{k-1})}{t_k - t_{k-1}}$$

$$\int_0^{t_k} y_l \, dt \cong y_l(t_k)(t_k - t_{k-1}) + \int_0^{t_{k-1}} y_l \, dt$$

Since not all measurements are taken at all times in the database, smoothing or fitting the measurements by interpolation will be used to place them on a single common time grid, e.g., linear spline, cubic splines, etc. The best method for smoothing, beginning with the simplest linear splines, will be examined.

The control input is one of M different control input that can be applied to the system.

Specifically, the control input, $u(t_k)$ at time $t_k$ is assumed to be drawn from the finite set, $$u(t_k) \in \{u_1, \ldots, u_m\} \quad (2.3)$$

The simultaneous administration of two or more types of therapy will be treated mathematically as a separate distinct mode of combination therapy. Hence M generally includes all single therapies plus relevant combinations of therapies, such as packed red cells and crystalloid fluids, fresh frozen plasma and transfusions.

It is convenient to think of the propagation of the patient's state $x_k$ at time $t_k$, to his state $x_{k+1}$ at time $t_{k+1}$ as obeying the following nonlinear dynamical system with process noise $w_k$ and parameters p, i.e.:

$$x_{k+1}^j = f(x_k^j, u_i, p, w_k) \quad (2.4)$$

For simplicity, p is discrete, and is assumed to be drawn from a finite set formed by enumerating all useful combinations of covariates, $$p \in \{p_1, \ldots, p_m\} \quad (2.5)$$

Both covariates and process noise help to explain the variability of patient responses seen in the database. The covariates help to distinguish gross differences in responses due to patients with major differences in the nature of their disorders and complications. Process noise helps to explain small differences between patients with the same covariates but different responses to the same therapy. It is a measure of unmodeled dynamics, or intra-individual variability, due to other sources of variability in the system.

The outcome predictor calculates the value PC or probability of survival.

For a given state x, the survival probability is denoted by S(x), which is calculated simply by extracting the N nearest neighbor states to x of patients having the same collection of covariates p (denoted as the set $\{x\}_{j=1}^N (x, p)$) and by calculating the fraction of them that survived. For example, if N s of the N nearest neighbor states to x survived, then the PC is given as, $$S(x) = N_s/N \quad (2.6)$$

This quantity is equivalent to the estimated survival probability, and is a useful measure of the severity of the patient's current illness.

A stochastic controller is shown in FIG. 3, which does not require a model, but which rather uses the patient database directly. When a new patient is admitted, the analysis and control (decision support) is calculated by the following operations.

Step 0. Take measurements at 3 distinct successive times to calculate a nominal state $x_0^0$ according to (2.2), and define a relevant covariate vector $p^0$. Define k=0 to initialize the algorithm at time zero.

Step 1. Given the nominal state $x_k^0$ and a covariate vector $p^0$, extract the N nearest-neighbor states (denoted as $\{x_k\}_{j=1}^N = N(x_k^0, p^0)$) that are closest to $x_k^0$ in the database and share the same covariates. Here, a measure of "closeness" is conveniently defined in terms of the quadratic distance, $$d(x, x_k^0) \equiv (x_k^0 - x)^T W(x_k^0 x) \quad (3.1)$$

where the weighting matrix W is taken to be diagonal, $$W = \text{diag}[w_1, \ldots, w_N] \quad (3.2)$$

The best choice of weighting matrix W remains to be investigated further.

Step 2. From the set of nearest-neighbors $\{x_k\}_{j=1}^N$ calculate the fraction of them which survived, to define $S(x_k^0)$.

Step 3. Sort the N nearest-neighbors states into m groups depending on the type of control input u, which was applied to it (as recorded in the database). This gives the group of sets, $$\{u_k^{ij}, u_i\}_{j=1}^{m_1}, i=1, \ldots, m \quad (3.3)$$

For example, the subgroup $\{x_k^{ij}, u_i\}_{j=1}^{m_1}$ denotes the subgroup of $m_1$ nearest-neighbor states which received a specific control (therapy) input of type i=1. Note that $$\sum_{i=1}^M m_i = N \quad (3.4)$$

since the state has a specific control associated with it.

Step 4. For each state $x_k^{ij}$ in the i'th subgroup, calculate the subsequent state $x_{k+1}^{ij}$ By moving to the next line in the database, i.e.

$$x_{k+1}^{ij} = f(x_k^{ij}, u_i, p, w_k) \quad (3.5)$$

Calculate the survival probability $S(x_{k+1}^{ij})$ associated with this new state (remember this requires extracting nearest neighbors to $x_{k+1}^{ij}$). Define the PC associated with the i'th control as $$P_k(u_i) = \frac{1}{m_i} \sum_{j=1}^{m_i} S(x_{k+1}^{ij}) \qquad (3.6)$$

Step 5. Apply u* to the patient, take new measurements (to define new state $x_{k+1}$), set k←k+1, and go to step 2.

An important feature of the above is the ability to defined the patient's unique "state" at any given time. I the database that is used preferably is a large database with multiple timelines describing clinical and hemodynamic patterns of subsets at different conditions. The states should be described in time that elapses from the onset of illness or from admission.

Weighting criteria to specify the nearest neighbors have been based upon the clinical diagnosis, co-morbid conditions, and hemodynamic patterns of survivors vs. nonsurvivors. For example, for the series as a whole, discriminant analysis revealed significant differences between survivors' and nonsurvivors' net cumulative deficits in $PtcO_2$/$FiO_2$ ($p<0.0001$), $SapO_2$ ($p<0.005$), CI ($p<0.03$), and the initial GCS value ($p<0.0001$). Further, we will use, as weighting criteria, the p values of differences in the temporal patterns of survivors' and nonsurvivors' values in each subset, for example, for subsets of patients with and without head injuries, blunt vs. penetrating trauma, truncal and nontruncal trauma, age stratifications, prior cardiac, respiratory, hepatic, and renal dysfunction or organ failure, etc. Finally, the hemodynamic responses to standardized test doses of whole blood or packed red cell transfusions given over a specified period of time (usually 1-hour) provide quantitative measures of each patient's cardiac reserve capacity. This is expressed as changes in cardiac index relative to corresponding change in PA occlusion (wedge) pressure or central venous pressure (Starling's myocardial performance curve) before and after a blood transfusion given over a one-hour period. Criteria for satisfactory vs. limited cardiac functional reserve capacity have been developed for each clinical subset and each time period.

In operation, the program has been used to evaluate individual patients states in terms of probability of survival based on initial baseline measurements. So far, all those with outcome probabilities >80 percent have survived and all those with probabilities less than 30 percent have died. At 300, the patients individual data is put into the database to determine theN nearest neighbors of the user. The survival probability is determined at 305, using the operator S. the patients are also sorted by control intervention at 310. The state response is propagated at 315, and at 320, the survival probability is calculated conditioned on intervention. Stochastic probability control is determined at 325.

The stochastic analysis and control program can be used for data mining to detect significant hemodynamic events and their relationship to therapy given. It will begin by tracing individual patient histories in the database through time, where at each instant, the "state" of the patient (see definition earlier) is computed, as well as the patient's associated probability of survival (based on nearest neighbors) before and after specific therapy. A large change, either up or down, in survival probability indicates a potentially significant role of the associated therapy. This flags the corresponding patient and time for a closer look at what is actually going on. The entire database will be processed this way, and statistics about the various significant events will be compiled. Therapeutic interventions with the most efficacy or harm can be flagged for more detailed analysis of the contribution of each therapeutic modality and each hemodynamic variable to each patient's survival or death.

Although only a few embodiment have been disclosed in detail above, other modifications are possible.

What is claimed is:

1. A system comprising:
   a monitoring device monitoring a plurality of physiological signals of a current patient;
   a database, which stores records indicative of a plurality of patients including at least some of said physiological signals for said plurality of patients and prognosis information for said plurality of patients;
   a processor, comparing said physiological signals to said stored records in a database, to determine mathematically patients in the database which are most similar to a current patient; and to make available information about treatment and results for said patients who are most similar to the current patient;
   wherein said physiological signals include hemodynamic information; and
   wherein said processor also carries out interpolation to place a plurality of said signals on a common time grid.

2. A method, comprising:
   monitoring a plurality of physiological signals of a current patient;
   comparing said physiological signals of the current patient to stored physiological signals for previous patients stored in a database;
   determining patients in said database who are most similar to the current patient;
   determining information about treatments and results for said patients who are most similar to the current patient,
   wherein said physiological signals include signals indicative of hemodynamic information;
   obtaining covariate information indicative of a patient's individual characteristics, and wherein the steps of determining most similar patients and of determining information are also based on said covariate information; and
   wherein said determining most similar patients comprises mathematically determining a state variable indicative of the current patient based on at least said hemodynamic information and said covariate information.

3. A method, comprising:
   monitoring a plurality of physiological signals of a current patient;
   comparing said physiological signals of the current patient to stored physiological signals for previous patients stored in a database;
   determining patients in said database who are most similar to the current patient;
   determining information about treatments and results for said patients who are most similar to the current patient;
   wherein said physiological signals include signals indicative of hemodynamic information;
   obtaining covariate information indicative of a patient's individual characteristics, and wherein the steps of determining most similar patients and of determining information are also based on said covariate information;

wherein said determining most similar patients comprises mathematically determining a state variable indicative of the current patient based on said hemodynamic information and said covasiate information; and wherein said determining a state variable comprises investigating derivatives of the hemodynamic information and integrals of the hemodynamic information.

4. A method, comprising:

monitoring a plurality of physiological signals of a current patient;

comparing said physiological signals of the current patient to stored physiological signals for previous patients stored in a database;

determining patients in said database who are most similar to the current patient;

determining information about treatments and results for said patients who are most similar to the current patient; and wherein said determining patient a comprises determining quadratic distances between a state variable representing the current patient and state variables representing other patients in said database.

5. A method as in claim 4, further comprising using a weighting matrix to determine said most similar patients.

6. A method as in claim 5, further comprising determining said weighting matrix based on hemodynamic parameters and survival versus non survival.

7. A method, comprising:

monitoring a plurality of physiological signals of a current patient;

comparing said physiological signals of the current patient to stored physiological signals for previous patients stored in a database;

determining patients in said database who are most similar to the current patient;

determining information about treatments and results for said patients who are most similar to the current patient; and wherein said comparing comprises interpolating among said physiological signals to evaluate said physiological signals on a common time scale.

8. A system comprising:

a monitoring device monitoring a plurality of physiological signals of a current patient;

a database, which stores records indicative of a plurality of patients including at least some of said physiological signals for said plurality of patients and prognosis information for said plurality of patients;

a processor, comparing said physiological signals which include hemodynamic information of the current patient to said stored records in the database, to determine mathematically patients in the database which are most similar to the current patient; and to make available information about treatment and results for said patients why are most similar to the current patient; and wherein said processor obtains covariate information indicative of a patient's individual characteristics, wherein said processor mathematically determines said similar patients by determining a state variable for a patient based on at least said hemodynamic information and said covariate information.

9. A system as in claim 8, wherein said state variable is defined as a vector over time, where each point in time includes measurements at that point in time.

10. A system as in claim 9, wherein said state variable also includes derivatives of the hemodynamic measurements and integrals of the hemodynamic measurements.

11. A system as in claim 9, wherein said state variable is also a function of non covariate parameters, and inconsistencies between said state variable are explained in terms of said covariate parameters.

12. A system as in claim 9, wherein said processor models said patient as a control system, with said state variable representing a patient's state, a control input representing a therapy, and the patient's state following a nonlinear dynamic system with process noise being explained in terms of covariate parameters.

13. A system as in claim 12, wherein said processor models said patient with a survival probability based on nearest neighbor states to other patients in the database.

14. A system as in claim 9 wherein said processor uses said state variable to find nearest neighbors in the database which represent patients that are most similar to the current patient.

15. A system as in claim 14, wherein said finding nearest neighbors comprises determining a quadratic distance between the current patient and other patients in the database.

16. A system as in claim 14, wherein said processor uses a weighting matrix to determine said closest neighbors.

17. A system as in claim 16, wherein said weighting matrix is based on relationships between hemodynamic patterns and survival versus non survival.

18. A method, comprising:

monitoring a plurality of physiological signals of a current patient;

comparing said physiological signals of the current patient to stored physiological signals for previous patients stored in a database;

determining patients in said database who are most similar to the current patient;

determining information about treatments and results for said patients who are most similar to the current patient; and wherein said determining information comprises modeling said patient as a control system with a state parameter representing a patient's state, a control input representing a therapy, and a nonlinear dynamic system, with process noise being explained in terms of covariate information indicative of a patients individual characteristics.

19. A method, comprising:

monitoring a plurality of physiological signals of a current patient;

comparing said physiological signals of the current patient to stored physiological signals for previous patients stored in a database;

determining patients in said database who are most similar to the current patient; and determining information about treatments and results for said patients who are most similar to the current patient, wherein said determining information comprises determining a likelihood that the patient will survive.

20. A method, comprising:

monitoring a plurality of physiological signals of a current patient;

comparing said physiological signals of the current patient to stored physiological signals for previous patients stored in a database;

determining patients in said database who are most similar to the currant patient;

determining information about treatments and results for said patiently who are most similar to the current patient, wherein said determining information comprises determining a therapy for the current patient which has proved most statistically successful for said patients who are most similar to the current patient.

21. A method, comprising:

determining hemodynamic characteristics of an individual patient;

determining covariate parameters of the individual patient representing the patient's individual characteristics;

using said covariate characteristics and said hemodynamic parameters to develop a state variable that represents information that is continuously variable in time;

comparing said state variable with information indicative of a plurality of previously treated patients in a database; and obtaining survival information about said patients in said database.

* * * * *

UNITED STATES PATENT AND TRADEMARK OFFICE
CERTIFICATE OF CORRECTION

PATENT NO.     : 6,896,660 B2
DATED          : May 24, 2005
INVENTOR(S)    : Roger Jelliffe et al.

It is certified that error appears in the above-identified patent and that said Letters Patent is hereby corrected as shown below:

<u>Column 1,</u>
Line 4, should read:
-- This invention was made with government support under Contract No. 5 R01LM05401-09 awarded by the National Institute of Health. The government has certain rights in the invention. --.

Signed and Sealed this

Sixteenth Day of August, 2005

JON W. DUDAS
*Director of the United States Patent and Trademark Office*